US007758893B2

(12) United States Patent
Hageman et al.

(10) Patent No.: US 7,758,893 B2
(45) Date of Patent: Jul. 20, 2010

(54) ENTERAL COMPOSITIONS FOR THE PREVENTION AND/OR TREATMENT OF SEPSIS

(75) Inventors: Robert Johan Joseph Hageman, Wageningen (NL); Gelske Speelmans, Wageningen (NL); Adrianus Johannes Maria Vriesema, Houten (NL)

(73) Assignee: N.V. Nutricia, Zoetermeer (NL)

( * ) Notice: Subject to any disclaimer, the term of this patent is extended or adjusted under 35 U.S.C. 154(b) by 1211 days.

(21) Appl. No.: 10/484,884

(22) PCT Filed: Jul. 26, 2002

(86) PCT No.: PCT/NL02/00510

§ 371 (c)(1),
(2), (4) Date: Jan. 27, 2004

(87) PCT Pub. No.: WO03/009704

PCT Pub. Date: Feb. 6, 2003

(65) Prior Publication Data

US 2004/0191263 A1 Sep. 30, 2004

(30) Foreign Application Priority Data

Jul. 27, 2001 (EP) .................................. 01202873

(51) Int. Cl.
*A61K 9/16* (2006.01)
*A61K 39/395* (2006.01)
*A61K 47/00* (2006.01)
*A61K 35/12* (2006.01)
*A61K 35/54* (2006.01)
*A01N 25/26* (2006.01)
*G01N 33/02* (2006.01)

(52) U.S. Cl. .................... 424/498; 424/130.1; 424/418; 424/420; 424/439; 424/520; 424/581; 436/21

(58) Field of Classification Search ................. 424/199, 424/365, 1.65; 514/549
See application file for complete search history.

(56) References Cited

U.S. PATENT DOCUMENTS 4,474,773 A * 10/1984 Shinitzky et al. .............. 514/78
5,434,183 A    7/1995 Larsson-Backstrom
5,550,146 A * 8/1996 Acosta et al. ................ 514/400
5,585,098 A * 12/1996 Coleman .................. 424/157.1
6,063,946 A    5/2000 Miller et al.
6,200,624 B1 * 3/2001 Mazer et al. ................ 426/590

FOREIGN PATENT DOCUMENTS

| DE | 43 10 935   | 11/1993 |
|----|-------------|---------|
| EP | 0 711 151   | 5/2000  |
| EP | 1 090 636   | 4/2001  |
| JP | 54-20174    | 2/1979  |
| JP | 8-187062    | 7/1996  |
| JP | 8-311482    | 11/1996 |
| JP | 10-237480   | 9/1998  |
| JP | 2000-504221 | 4/2000  |
| WO | WO 91/14454 | 10/1991 |
| WO | WO 98/00110 | 1/1998  |
| WO | 00/03660    | 1/2000  |
| WO | 01/19356    | 3/2001  |
| WO | 01/28555    | 4/2001  |

OTHER PUBLICATIONS (Webster's II New Riverside University Dictionary), definition of sepsis.*
Hobart W. Harris et al., "Chylomicrons Alter the Fate of Endotoxin, Decreasing Tumor Necrosis Factor Release and Preventing Death", The Journal of Clinical Investigation, Inc., Mar. 1993, pp. 1028-1034, vol. 91.
M. Mahmood Hussain et al., "A proposed model for the assembly of chylomicrons", Atherosclerosis, 2000, pp. 1-15, vol. 148, Elsevier Science Ireland Ltd.
Yvon A. Carpentier, "Actions immunomodulatrices des lipides", Nutr. Clin. Metabol., 1996, pp. 97-105, vol. 10.
John E. Kinsella et al., "Dietary lipids, eicosanoids, and the immune system", Critical Care Medicine, 1990, pp. S94-S113, vol. 18, No. 2, The Williams & Wilkins Co.
Thomas E. Read et al., "Triglyceride-rich Lipoproteins Prevent Septic Death in Rats", The Journal of Experimental Medicine, Jul. 1995, 267-272, vol. 182.

* cited by examiner

*Primary Examiner*—Vanessa L. Ford
(74) *Attorney, Agent, or Firm*—Young & Thompson

(57) ABSTRACT

The present invention relates to an enteral composition containing phospholipids, triglycerides and cholesterol or precursors thereof, which can be used in the treatment of sepsis. With the composition of the invention the natural level of chylomicrons is maintained, in particular in gut associated lymphoid tissue (GALT), which ensures that most of LPS and/or LTA which are released in the body can be neutralized, substantially decreasing the risk of locally occurring high levels of LPS and/or LTA and thus sepsis.

29 Claims, No Drawings

ENTERAL COMPOSITIONS FOR THE PREVENTION AND/OR TREATMENT OF SEPSIS

TECHNICAL FIELD OF THE INVENTION

The present invention relates to an enteral composition and use thereof containing phospholipids, triglycerides and cholesterol or precursors thereof for the prevention and/or treatment of sepsis.

BACKGROUND OF THE INVENTION

Sepsis is a disorder which occurs when a relative large amount of micro-organisms or fragments thereof enters the body. It is also referred to as endotoxemia or endotoxic shock. Endotoxin, or lipopolysaccharide (LPS) is a component of the outer cell membrane of Gram-negative bacteria. Lipoteichoic acid (LTA) is a component of the outer membrane of Gram-positive bacteria that can also give rise to sepsis. The intestines, especially the colon, are a reservoir of LPS and Gram-negative bacteria, such as the common inhabitant *Escherichia coli*, but also of LTA and Gram-negative bacteria. LPS as well as LTA can enter the systemic circulation by direct translocation from the gut or via translocation of Gram-negative and/or Gram-positive bacteria across the intestinal wall.

The presence of Gram-negative and/or positive bacteria and LPS and/or LTA in the gut is of no problem for a healthy person. However, in persons or animals with imparted barrier function of the gut, for instance caused by ischemia, surgery, chronic inflammation, radiotherapy, trauma, use of certain drugs, such as NSAID's or chemotherapeutics, critically ill persons such as persons under intensive supervision, or persons infected by invasive pathogens, LPS, LTA, Gram positive bacteria and/or Gram-negative bacteria can cross the intestinal wall and reach the circulation. Once these bacteria have entered the system, LPS and/or LTA are released, which release is mainly due to a high activity of the phagocytic system. This infection process can also occur via the lungs (or during infections) or via peripheral body parts (e.g. after traumata caused by accidents, or during decubitus, during the last phases of some pregnancy disorders (HELLP syndrome) or during transfusions).

The release of LPS and/or LTA in the body can lead to an acute phase response and sepsis if LPS and/or LTA are not properly neutralized. Such unproper neutralisation may occur in animals/persons with a compromised immune function, as is often the case after malnutrition, fasting, surgery, ischeamic conditions, severe burn injury, chronic infection, cancer therapy, imparted liver or spleen function, with critically ill persons, and also with persons that have to recover directly after severe surgery.

The acute phase response can be determined by measuring levels of C reactive protein in blood. C-reactive protein is an acute phase protein in man and an important component of the innate immune system. C-reactive protein activates the classical pathway of complement, which is one of its main mechanisms in providing host defense. It has recently been recognized that C-reactive protein interacts with the cells of the immune system by binding to Fc gamma receptors. It may thus bridge the gap between innate and adaptive immunity and provide an early, effective antibacterial response. Furthermore, as it protects against the damaging inflammatory response to lipopolysaccharide and cytokines, it may prevent the lethal side-effects of bacterial products. Risk of sepsis can be determined by measuring in vivo protein synthesis in cells of the immune system such as T lymphocytes as described in Januszkiewicz et al. Clin. Nutr. 2001, 20(2), 181-182.

Sepsis can lead to multiple organ failure or death. It is therefore of great importance to find a method to treat, and especially prevent sepsis. Several approach have been proposed in the prior art to alleviate the symptoms or prevent or treat sepsis.

One approach has been given in WO 98/32428 which describes the use of choline in an enteral feeding for the reduction and/or prevention of endotoxin induced injury and mortality. The amount administered is 1.5 to 20 g per day. Choline is administered as choline tartrate.

Another approach has made use of phospholipids such as given in U.S. Pat. No. 5,434,183 which describes phospholipids containing ω-3 fatty acids DHA and EPA in combination with vegetable oil and/or marine oil for anti-inflammatory and/or immunosuppressive effects in the treatment of rheumatoid arthritis and sepsis. This enables the obtention of a very low level of serum cholesterol and serum triglycerides.

WO 96/04916 describes protein and peptide free intravenous injection preparations containing at least one phospholipid in combination with cholanoic acid or cholanoic acid salt for the prophylaxis and therapy of endotoxin related conditions. Optionally a neutral lipid can be added.

JP 05320043 describes a lipopolysaccharide scavenger consisting of phospholipids, in particular phosphatidyl choline, cholesterol and saturated fatty acids, in particular myristic acid. These components are converted into liposomes which are used in a solution for intravenous administration for prevention or treatment of ischemia or tissue injuries after ischemia. A suitable concentration ratio of cholesterol to phosphatidyl choline to myristic acid is 5-10:5-10:1-5.

U.S. Pat. No. 4,474,773 also describes the administration of the combination of phospholipids, triglycerides, and cholesterol for treating, among others, dysfunctions of the immune system, the administration according to U.S. Pat. No. 4,474,773 being advantageously made intravenously.

The drawback of the compositions of the prior art for treating sepsis is that the formulations are complex, e.g. a liposome. A further drawback is that parenteral administration is intended which poses a greater risk to the patient. There is thus a need for a relatively simple, effective, safe preparation for the prevention and treatment of sepsis.

It has now been found that sepsis can be effectively prevented and/or treated by means of an enteral composition comprising phospholipids, triglycerides and cholesterol or precursors thereof.

The present invention is based on the finding that LPS and/or LTA are detoxified in the circulation by incorporation into lipoproteins such as LDL (Low Density Lipoprotein), VLDL (Very Low Density Lipoprotein), chylomicrons and HDL (High Density Lipoprotein), in particular chylomicrons. It is believed by the inventors that chylomicrons play an important role in absorbing and transporting lipophilic substances in general such as food components and toxins (e.g. LPS and/or LTA), which can enter the body via the intestine but which can also be formed in case of elimination of remnants of dead bacterial cells in parts of the body. Chylomicrons are released in the gut associated lymphoid tissue (GALT) and take up LPS and/or LTA that are released after lyses of bacteria in the enterocytes and in particular in the lymph nodes. The chylomicrons are transported from the lymph nodes via the ductus thoracicus to the angulus venosus sinister, which transports the chylomicrons, and other lipoproteins, to the heart, which then transports them to the Reticulo Endothelial System (in particular the spleen) and the liver (Kupffer cells). Chylomicrons can thus also be used as a vehicle for delivery in the liver of lipid soluble substances, thereby preventing losses which can occur from malabsorption.

Maintaining the natural level of chylomicrons, not only in blood plasma, but especially in GALT e.g. over a relatively large part of the length of the gut, ensures that most of the LPS and/or LTA which are released in several locations of the body e.g. in the lungs or gut, can be neutralized, substantially decreasing the risk of locally occurring high levels of LPS and/or LTA.

In view of these findings, it is thus essential according to the invention, contrary to the prior art, to administer the combination of phospholipids, triglycerides, and cholesterol as an enteral composition and not an intravenous composition. The combination of phospholipids, triglycerides and cholesterol is digested in the intestine ensuring a relatively constant release of chylomicrons for a prolonged period of time in GALT since the product is relatively slowly digested. Further, the combination of phospholipids, triglycerides and cholesterol of the invention has the advantage that the ingredients used need no specific pretreatments such as liposome formation which results in an effective product with a relatively low cost price. Further, enteral administration of the composition is simple and safe.

Compared to U.S. Pat. No. 4,474,773 which provides the intravenous administration of phospholipids, triglycerides and cholesterol, it has now been found, as above explained, that the enteral administration favors the formation of chylomicrons in GALT, thereby providing effective prevention and/or treatment of sepsis. In this respect, it is believed that the teaching of U.S. Pat. No. 4,474,773 would be detrimental to such prevention and/or treatment. Indeed, U.S. Pat. No. 4,474,773 provides the stimulation of the immune system by increasing the lymphocyte production. However, a problem encountered with this stimulation is that cytokines are in turn produced, which latter components are involved in the pro-inflammatory response that underlies sepsis (Intensive Care Med. 200;26 Suppl. 1:S124-8, Immunomodulatory therapy in sepsis, Kox W. J. et al.). This is further confirmed by Inflamm. Res. 1998 May; 47(5):201-10, "The inflammatory basis of trauma/shock associated multiple organ failure", Yao Y. M. et al, which describes that activation of the immune system may produce a generalized inflammation finally leading to sustained inflammation and multiple organ damage. Accordingly, though following the teaching of U.S. Pat. No. 4,474,773, a stimulation of the immune system would be provided, this would nevertheless be detrimental to the treatment and/or prevention of sepsis.

Wang X. D. et al describe in Scand. J. Gastroenterol 1994: 1117-1121 that the enteric administration of phospholipids significantly reduced the incidence of bacterial translocation after 90% hepatectomy in rats. They describe that bacterial translocation under certain conditions may cause sepsis or bacteremia. It is then concluded that the decrease in bacterial translocation is probably the result of phospholipids nourishing the intestinal mucosa and maintaining the intestinal barrier or by preventing of the barrier function as mucosal surfactant. However, this article makes no mention of chylomicrons, let alone of its relation with the prevention or treatment of sepsis.

Still another approach has been given by WO 01/19356 which prescribes the enteral administration of the combination of medium chain triglycerides and lipid to prevent sepsis.

SUMMARY OF THE INVENTION

According to one aspect of the invention, there is provided the use of phospholipids, triglycerides and cholesterol or precursors thereof in the preparation of an enteral composition for the treatment and/or prevention of sepsis.

According to another aspect of the invention, there is provided an enteral composition comprising phospholipids, triglycerides and cholesterol, wherein the composition comprises from 45% to 91% by weight of the composition of phospholipids.

According to a further aspect of the invention, there is provided an enteral composition comprising phospholipids, triglycerides and cholesterol, wherein the cholesterol is present within the composition in an amount of from 0.5% to 3% by weight of the composition.

DETAILED DESCRIPTION OF THE INVENTION

An essential element of the present invention is a phospholipid. Phospholipids for use herein are selected from phosphatidyl choline, phosphatidyl ethanolamine, phosphatidyl inositol, phosphatidyl serine, phosphatidyl glycerol, phosphatidic acid, and mixtures thereof.

Preferably, the phospholipids are administered as a mixture of phospholipids, in particular comprising phosphatidyl choline and one or more of phosphatidyl ethanolamine, phosphatidyl inositol, phosphatidyl serine, phosphatidyl glycerol, and phosphatidic acid. More preferably, the composition contains at least phosphatidyl choline and phosphatidyl ethanolamine.

Typically, phospholipids for the purpose of the present invention will be present in an amount of from 45% to 91% by weight of the composition. Still, it has now also been found that the presence of a high level of phospholipids in the invention composition further increased the formation of chylomicrons, and thus further improved the prevention and/or treatment of sepsis. Accordingly, it is preferred when phospholipid is present in high amount that a level of from 48% to 78%, more preferably of 55% to 69 wt % of phospholipids is used or present in the invention composition. However, when triglycerides is desired as predominant component, the level of phospholipids within the composition is then preferably of from 10 to 45% by weight of the composition.

As a source of phospholipids, preparations enriched in a particular phospholipids or containing relatively pure (synthetic) phospholipids can be used. Though after consumption of synthetic phospholipids and even lysophospholipids chylomicrons are formed in vivo, it is preferred to use natural sources, in particular egg and soy lecithin. Indeed, these are more economical, are favored by consumers but also can sometimes be more stable. The following natural sources of phospholipids have been found very suitable:

- A preferred soy lecithin for use herein contains, based on total phospholipid content, 35 to 50 wt. % phosphatidyl choline and 25 to 40 wt. % phosphatidyl ethanolamine.
- A preferred egg phospholipid extract for use herein comprises 50 to 70 wt % phosphatidyl choline and 15 to 22 wt % phosphatidyl ethanolamine.
- The fatty acids in the phospholipids in particular comprise less than 30% docosahexaenoic and/or eicosapentaenoic acid.

Phospholipids are administered in an amount of 0.01 to 1.5 gram per kilogram body weight per dose. For humans this results in about 0.6 to 80 g per dose. As described above doses are administered at least once every 24 hours, but preferably every 2-12, more preferably every 3-8 hours or even on a continuous basis.

The daily dose of phospholipids is chosen in such a way that it results in either restoring the lipoproteins from low levels to levels observed in healthy well fed persons or even enhancing the levels in a short period of time to 120% or even above 150%, compared to a healthy person and/or to enhance the phospholipid/lipoprotein ratio in the blood. Indeed, it has been found that it is preferred to have a weight/molar ratio which is high in favor of the phospholipids. Chylomicrons (and other lipoproteins) containing a high amount of phospholipids will have a higher capacity in neutralising endotoxin. Furthermore, a high amount of phospholipids will aid in absorption of triglycerides and also improve the gastrointestinal barrier function.

In particular, the phospholipid dosage is preferably specific to the type of patient as well as to the type of administration. Thus, three groups of patients can be defined:

Group 1, which are patients who can be fed with enteral nutrition and who consumes triglycerides and cholesterol on a regular basis;

Group 2, which are malnourished patients or with imparted metabolic capacity in the enterocytes;

Group 3, which are extremely weak patients typically fed by parenteral ways.

Patients from Group 1 and 2 would benefit from the various types of nutrition. However, it has been found that when long term tube feeding is used, it is preferred to use the invention composition which is predominant in triglycerides (i.e. more than 50% by weight) because the lipids that are present in the gut are provided from the composition administration. Accordingly, for a complete enteral nutrition composition and considering a consumption of 2000 kcal a daily dosage of phospholipids for long term tube feeding is preferably of from 4-30 g, more preferably 6-28 g.

When short term tube feeding is used, it is preferred to use the invention composition which is predominant in phospholipids as residual triglycerides can still be present in the gut provided from earlier meals and as the cholesterol synthesis in enterocytes would then not be strongly imparted. Accordingly, for a complete enteral nutrition composition and considering a consumption of 2000 kcal, a daily dosage of phospholipids for long term tube feeding is preferably of from 20-75 g, more preferably 28-60 g.

When a supplement is used, it has been found that group 1 and 2, although to a less extent for group 2, would benefit from a supplement that is predominant in phospholipids (i.e. above 45% by weight) as this would enable group 1 patients to consume a regular diet of triglycerides and cholesterol whereas for group 2 patients, this would enable them to consume the essential elements to their organism. Accordingly, for a supplement composition predominant in phospholipids and considering a consumption of 200-600 ml and a lipid content of about 5%, a daily dosage of phospholipids for a supplement is preferably of from 5-28 g, more preferably 15-25 g, whereas for a supplement composition predominant in triglycerides, a daily dosage of phospholipids for a supplement is preferably of from 1-13 g, more preferably 2-8 g.

It was further found that supplement on group 3 patients would be beneficial by administering small quantities (50-400 ml) of the invention composition predominant in triglycerides.

Another essential element of the present invention is a triglyceride. Triglycerides of the invention are in particular selected from glycerol esterified with long chain fatty acids. With long chain fatty acids, fatty acids are meant with at least 18 carbon atoms. The amount of long chain fatty acids related to the total amount of fatty acids in the triglyceride, should be at least 50% and preferably more than 60% in order to observe significant chylomicron formation in vivo. Preferred long chain fatty acids are stearidonic, oleic, α-linolenic, linoleic, gamma-linolenic, conjugated linoleic acid, docosahexaenoic, eicosapentaenoic and arachidonic acid. More preferably, polyunsaturated fatty acids are used which result in more efficient chylomicrons, i.e. in chylomicrons which are more suitable to scavenge LPS and/or LTA. The amount of myristic acid in the triglyceride fraction is preferably smaller than 40%, more preferably smaller than 25 wt. %.

Examples of triglycerides are vegetable oils such as soy oil, corn oil, olive oil, sunflower oil, sesame oil, safflower oil, wheat germ oil, arachidic oil, evening primrose oil, egg oil, or mixtures thereof, but also marine oils, such as fish oil and algal oil are suitable, optionally mixed with one or more vegetable oils.

Typically, triglycerides for the purpose of the present invention will be present in the mixture of triglycerides, cholesterol and phospholipids in an amount of at least 7% to less than 80 wt. %. Still, it is preferred when phospholipid is present in high amount that a level of from 7% to 50 wt % of triglycerides is used or present in the invention composition. However, when triglycerides is desired as predominant component, the level of triglycerides within the composition is then preferably of more than 50 to 80% by weight of the composition.

The dose of triglycerides is 0.01 to 1 g/kg body weight. This results in administration of about 0.6 to 60 g triglycerides per dose to diseased humans.

Still another essential element of the present invention is cholesterol or its precursor thereof. Indeed, the presence of cholesterol in addition to the presence of phospholipids and triglycerides has been found beneficial to the combination in the sense that more chylomicrons were produced than with the only combination of phospholipids and triglycerides, thus in turn providing better prevention and/or treatment of sepsis.

In particular one or more of cholesterol or cholesteryl esters like those that occur in natural extracts (egg) and synthetic sources like esters with organic acids, e.g. cholesteryl acetate, hemisuccinate, n-butyrate, oleate, or with phospholipids are used. Preferably, a cholesterol-rich fraction isolated from egg is used.

Typically, cholesterol or equivalents thereof for the purpose of the present invention will be present in the mixture of triglycerides, cholesterol and phospholipids in an amount of from 0.5% to 8% by weight of the composition. Still, it has also been found that when cholesterol was present within the specific range of from 0.5 wt. % to 3 wt. %, preferably 0.7 to 1.5%, the best response in terms of stability of the composition, especially when soy lecithin is used, and production of chylomicrons was obtained. Invention composition comprising egg cholesterol and egg lecithin have sometimes a tendency to an undesired creaming of the composition. Use of such specific cholesterol level combined with soy derived phospholipids has been found to provide a remedy to this problem.

The dose of this ingredient, calculated as cholesterol is preferably 2 mg to 120 mg per kg body weight per dose, preferably of from 14 mg to 80 mg per kg body weight per dose, resulting in a dose of 0.1 to 7 g in humans, preferably of from 1 to 5.5 g per dose.

The components of the composition of the invention (cholesterol, phospholipids and triglycerides) are present in their natural form or as separate ingredients. This means that liposomes are not envisaged by the invention.

In the preparation of the invention the weight ratio of cholesterol to phospholipids to triglycerides is preferably 1:3-80:3-90, more preferably 1:3-20:3-90, more preferably 1:6-16:6-60, most preferably is 1:6-12:12-40.

Still, as described hereinbefore, it is preferred for the purpose of the invention when a high amount of phospholipids is present resulting in a weight ratio of cholesterol to phospholipids to triglycerides of 1:20-80:3:80, more preferably of 1:20-75:20:75.

As a source for the combination of phospholipids, cholesterol and triglycerides of the invention eggs such as egg in the form of egg oil or egg powder can also be used. Eggs, in particular the lipid fraction thereof, already contain the desired components. Depending on the end use of the composition and the type of lipid extract that is used, all or some of the components (cholesterol, phospholipids and triglycerides) need to be supplemented to fall within the ranges indicated, such that the diet of the patients contains the right amounts of these components. It is particular advantageous if eggs are used of animals having a specific lipid mixture in their feed, which eggs have an increased content of $\alpha$-linolenic acid, conjugated linoleic acid and docosahexaenoic acid.

Besides that it contains the suitable components of the invention, eggs also have the advantage that they contain beneficial proteins. The protein fraction of eggs contains immunoglobulins which can interact with bacteria. The presence of immunoglobulins, in particular IgY, together with the components of the invention in the intestine, provides a very efficient system which prevents that bacteria translocate through the intestinal wall.

It is preferred that these immunoglobulins, in particular IgY, have been made suitable to bind to specifically those bacterial strains which form the greatest risk for causing sepsis. Such immunoglobulins can be induced in birds and transferred to eggs according to methods known in the art. A particular suitable product to be used according to the invention is thus hyperimmunized egg, which can be used as such after a light pasteurization, which keeps the immunoglobulins predominantly in undenatured and active state.

The composition preferably contains at least 0.02 g, preferably 0.08 to 1.6 g, more preferably 0.08 g to 0.9 g proteins per dose per kg body weight.

When proteins are used that originate from eggs of hyperimmunized birds, the daily dose of IgY that can be administered is then preferably of from 0.2 to 120 mg. Still, as the effectivity of the IgY when combined with invention composition has been found to improve the prevention of the bacteria translocation, the daily dose of IgY that can be administered is more preferably within the range of from 0.2 to 800 mg, most preferably of from 10 to 600 mg. The dose of this ingredient is preferably 0.1 mg to 10 mg per kg body weight per dose.

The doses for the treatment of the human/animal as described in the present application are given as dose per kg body weight. The amount for a dose can thus be determined based on the weight of the subject to be treated. The daily doses can be calculated by multiplying the dose with the number of times that the dose is consumed per day. The dose regime should be adjusted to maintain a high level of chylomicrons in the lymph e.g. by repeating dosing every 2-12 hours, preferably 3-8 hours or even on a continuous basis. For a group of patients tube feeding in the gut is recommended.

The enteral composition can further contain lactic acid bacteria, products of lactic acid bacteria, prebiotics, extra L-glutamine and/or L-arginine, fibres, carbohydrates, polysaccharides, vitamins, minerals such as zinc which will promote the adsorption of lipid-soluble substances, and other components as normally present in an enteral feeding.

In particular the composition contains fat soluble substances. These are in particular selected from vitamin K (menaquinones), ubiquinones, carotenoids such as vitamin A, specific fatty acids such as conjugated linoleic acid, lipoic acid and vitamin D. Inclusion of one or more of these components in the lipid mixture of the invention effectively decreases the prevalence of sepsis, decreases acute phase response and improves recovery after surgery or trauma When they are included in an enteral product together with the lipid mixture of the invention and optionally with zinc salt, lower amounts of these fat soluble substances than those in the prior art can be effective.

It is also preferred to incorporate berberin or extracts of *Berberis aristata* or *Coccinia fenestratum* in the preparation in an amount of 10-100, preferably 20-50 mg/kg body weight per dose.

The enteral composition of the invention is preferably used in the prevention and/or treatment of sepsis, bacteremia and/or endotoxaemia (endotoxic shock) and to delay acute phase response. In particular the composition is used for treatment of patients undergoing major surgery, critically ill patients, patients with Inflammatory Bowel disease (IBD), patients with HELLP syndromes, patients with an enhanced risk for bacterial translocation and sepsis in general, in particular those suffering from major trauma, burns, pneumonia, especially caused or complicated by bacteria., decubitus, during radio/chemo therapy or having a compromised immune system such as premature infants or elderly diseases.

In case of surgery, it is believed that the risk of endotoxaemia is related to the fact that patients need to fast preoperatively and that after surgery take only little food. As a result, the normal amount of chyloricrons is diminished, which makes them more vulnerable for damage caused by LPS. Generally these patients can take the composition of the invention until about 3 hours before surgery and shortly after surgery, but also the option of taking the composition during a shorter period before surgery is envisaged by the invention. In this case the total lipid level in the composition will typically be in the range of 5 to 70, preferably 15 to 50 g per dose. This dose can be supplied by means of a supplement for oral use, preferably a liquid in a relatively low volume, for example 100 to 700, preferably 150 to 600 ml.

The composition can also be taken by persons that allow intake of a restricted volume, such as persons suffering from anorexia nervosa or persons in the end stages of diseases such as cancer or AIDS, but also many elderly people. In this case the triglyceride level in the composition will be in the range of 0.7 to 30, preferably 2 to 15 g/dose, administered in a relatively low volume.

Mammals in general which are susceptible to infections, such as due to irregular feed regimes, e.g. cows and pigs, in particular weaning pigs, which can result in lower meat quality, can also be treated with the composition of the invention. Stress during transport can also result in bacterial translocation in animals.

The enteral composition of the present invention can be an oral or tube feeding, preferably a tube feeding. The oral feeding can be a complete feeding or a feed supplement, in liquid form or as a capsule or powder. Preferred liquid forms are dispersions. Intravenous compositions for the reasons explained hereinbefore are excluded from the invention.

Thus the invention also provides an enteral feed containing (dose)

8-120 g, preferably 12-80 g of the combination of cholesterol, phospholipids and triglycerides 5-100 g, preferably 12-60 g of a protein fraction and 1.2-400 g, preferably 5-200 g of a carbohydrate fraction.

Examples of enteral feedings are feedings that can be administered via a tube to a patient, for instance undergoing cardiosurgery, containing 0.5% to 7%(w/v), preferably 3 to 6% %(w/v) phospholipids in the presence of proteins, fat, sugars, fibrous and other components which are normally present in a complete enteral feeding. The feeding is started 24 hours before the surgery, which depending on the condition of the patient can be either by sip-feeding or tube-feeding, and is continued during 24 to 72 hours after the surgery via tube. Tube-feeding can also be carried out directly into the duodenum, thereby advantageously maintaining an empty stomach and preventing aspiration during surgery. Continuous treatment with the invention composition is an important and preferred aspect of the present invention. Indeed, continuous treatment, i.e. starting before operation, if any, and continuing for 4 to 5 days, provides a sustained production of chylomicrons, thereby providing a better and long lasting resistance against microbial infections, in particular those giving rise to sepsis.

A capsule or powdered food supplement containing the lipid mixture according to the invention is given to people with inflammatory bowel disease. The supplement may further contain fibers, oligosaccharides, vitamins, in particular fat soluble vitamins, as indicated above, probiotics, anti-oxidants, herbal or plant extracts, proteins or peptides, etc. The supplement is given to patients in remission in order to prevent recurrence of inflammation or to alleviate the inflammation once it re-occurs.

A liquid sip feeding with a phospholipid (why only phospholipids) concentration of 1-5% (w/v) can for instance be administered to a patient with obstructive jaundice, who will undergo surgery. In the feeding proteins, fats, polysaccharides and micronutrients may be present. The feeding is administered 24-12 hours before surgery and continues as soon as possible after surgery for 24 to 72 hours.

The composition of the invention is also suitable for newborn and premature children or animals.

The following are non-limiting examples illustrating the present invention:

EXAMPLE 1

Complete feeding containing per 100 ml:

| Energy | 125 kcal |
| --- | --- |
| Protein | 6 g (3 g egg white protein, 3 g whole milk protein) |
| N-acetyl cystein | 0.04 g |
| lipids | 4.5 g including: |
| | phospholipids 1.2 g |
| | triglycerides 3.1 g |
| | cholesterol 0.2 g |
| Carbohydrates | 15.5 g |
| Fiber | 0.2 g | minerals, trace elements and vitamins as known in the art

| vitamin K | 30 μg |
| --- | --- |
| coenzyme Q10 | 5 mg |

-continued

| tocopherols | 1 mg αTE |
| --- | --- |
| carotenoids | 0.1 mg |

EXAMPLE 2

Liquid feeding to be used as a supplement containing per 100 ml

| Energy | 100 kcal | |
| --- | --- | --- |
| protein | 9 g | |
| lipids | 2.1 g including: | |
| | phospholipids | 0.9 g |
| | vegetable oil | 1.05 g (sesame oil and olive oil (1:3)) |
| | cholesterol | 0.36 g |
| carbohydrates | 11.4 g | | minerals, trace elements, vitamins and other components as known in the art, for instance Na, K, Cl, Ca, Mg, Fe, Cu, P, Zn, I, vit. A, D, C, E, B1, B2, B6, B12, folic acid, pantothenic acid, niacine, biotine.

EXAMPLE 3

Tube feeding containing per 100 ml

| Protein (casein) | 4.0 g |
| --- | --- |
| Carbohydrates | 12.3 g |
| Fat | 3.9 g comprising 1 g phospholipid, 2.9 g triglycerides and 32 mg cholesterol | amounts according to the general guidelines on food for vitamins, minerals, choline, and trace elements are included

EXAMPLE 4

Egg Preparation

Hens are made hyperimmune by injecting them, when they are still pullets, one or more times with an extract of human pathogens that are known to play a role in sepsis. Eggs are collected and the whole contents are manufactured as described in the prior art in order to obtain a pasteurized and spray dried product that is rich in immunoglobulins against these pathogens, in particular IgY. A suitable method can be found in U.S. Pat. No. 5,585,098.

EXAMPLE 5

The liquid egg according to example 4 could also be extracted in order to obtain the lipid fraction and an IgY enriched fraction using a method as described in Juneja L. R., Egg Yolk lipids, CRC Press 1997, 0-8493-4005, page 73-98.

EXAMPLE 6

A liquid product is manufactured that comprises per 400 ml
16 g whole milk protein
8 g safflower oil
2 g corn oil
1 g deodorized fish oil
8 g lecithin 1 g cholesterol (5% wt on mixt lipid)
30 g maltodextrines
amounts according to the general guidelines on food for vitamins, minerals and trace elements are included

EXAMPLE 7

Preparation for Surgery Patients
A liquid preparation is manufactured that comprises per 400 ml
20 g egg white protein
24 g egg oil
25 g maltodextrines
800 μg folic acid
100 μg vitamin B12
3 mg pyridoxine
40 mg zinc sulphate
amounts according to the general guidelines on food for vitamins, minerals and trace elements are included

EXAMPLE 8

Nutritional Supplement for Cancer Patients
Bar used as snack having a salty and herb taste
Per 25 g the bar comprises
6 g egg lipids comprising per 100 g fatty acids >0.5 g DHA and >1.7 g AA, 400 μg folic acid
5 μg cyanobalamin
2 mg pyridoxin
2 g egg protein
200 μm magnesium carbonate
15 mg zinc oxide
100 mg calcium sulphate
About 2 g additives to give a salty or herb taste.
Make up with glucose syrup to 25 g and manufacture the bar as known in the art.

EXAMPLE 9

Formula for premature infants containing per 100 ml ready to use formula prepared according to methods known in the art:
1.2% protein of whole milk
3.0% of a fraction consisting of
  78% of a mixture of vegetable oils
  20% soy phospholipids
  2% cholesterol
8% carbohydrates including lactose
80 μg RE Vitamin A
20 μg Vitamin K

EXAMPLE 10

Preparation for Persons that Suffer from Severe Diarrhea
Bar used as snack having a salty and herb taste
Per 25 g the bar comprises
8 g whole egg powder
400 μg folic acid
5 μg cyanobalamin
2 mg pyridoxin
200 μm magnesium carbonate
15 mg zinc oxide
100 mg calcium sulphate
0.2 mg vitamin K
0.2 mg RE vitamin A
About 2 g additives to give a salty or herb taste.
Make up with glucose syrup to 25 g and manufacture the bar as known in the art.

EXAMPLE 11

Tube feeding containing per 100 ml

| Protein | 7.5 g |
| --- | --- |
| Carbohydrates | 14.5 g |
| Fat | 4.17 g comprising 1 g phospholipids and 21 mg cholesterol | amounts according to the general guidelines on food for vitamins, minerals, choline, and trace elements are included.

The invention claimed is:
1. An enteral composition comprising phospholipids, triglycerides and cholesterol or cholesterylester and/or a salt thereof, suitable for the treatment of sepsis, endotoxemia and/or bacteremia, wherein the composition comprises from 45% to 91% by weight of the composition of phospholipids, from 0.5% to 1.5% by weight of the composition of cholesterol, and wherein the weight ratio of cholesterol to phospholipids to triglycerides is 1:3-80:3-90.

2. The composition according to claim 1, wherein the phospholipids are in the form of a mixture of phospholipids comprising phosphatidylcholine and one or more of phosphatidylethanolamine, phosphatidylinositol, phosphatidyl serine, phosphatidyl glycerol, and phosphatidic acid.

3. The composition according to claim 1, wherein the triglycerides contain at least 50% long chain fatty acids with at least 18 carbon atoms, in particular long chain polyunsaturated fatty acids with at least 18 carbon atoms.

4. The composition according to claim 1, wherein the triglycerides are selected from vegetable oils, marine oils, and mixtures thereof, selected from soy oil, corn oil, olive oil, sunflower oil, sesame oil, safflower oil, wheat germ oil, arachidic oil, evening primrose oil, egg oil, fish oil, algal oil and mixtures thereof.

5. The composition according to claim 1, wherein the weight ratio cholesterol to phospholipids to triglycerides is 1:3-20:3-90.

6. The composition according to claim 5, wherein the weight ratio cholesterol to phospholipids to triglycerides is 1:6-16:6-60.

7. The composition according to claim 1, wherein the weight ratio cholesterol to phospholipids to triglycerides is preferably 1:20-80:3-80.

8. The composition according to claim 7, wherein the weight ratio cholesterol to phospholipids to triglycerides is 1:20-75:20-75.

9. The composition according to claim 1, wherein the composition contains egg, an egg lipid fraction, or an egg protein fraction.

10. The composition according to claim 1, wherein the composition further contains immunoglobulins.

11. The composition according to claim 1, wherein the composition contains soy lecithin.

12. The composition according to claim 1, wherein the composition is an oral feeding, tube feeding or infant formula.

13. The composition according to claim 1, wherein the composition further contains proteins or peptides.

14. The composition according to claim 1, wherein the composition further contains one or more fat soluble substances, selected from vitamin K, ubiquinones, carotenoids such as vitamin A, specific fatty acids such as conjugated linoleic acid, lipoic acid, vitamin D and mixtures thereof.

15. A unit enteral feeding composition, suitable for the treatment of sepsis, endoxemia and/or bacteremia, containing 8-120 grams of the combination of cholesterol, phospholipids and triglycerides, wherein the weight ratio of cholesterol to phospholipids to triglycerides is 1:3-80:3-90; 5-100 grams of a protein fraction; and 1.2-400 grams of a carbohydrate fraction.

16. The composition according to claim 15, wherein the phospholipids are in the form of a mixture of phospholipids comprising phosphatidylcholine and one or more of phosphatidylethanolamine, phosphatidylinositol, phosphatidyl serine, phosphatidyl glycerol, and phosphatidic acid.

17. The composition according to claim 15, wherein the triglycerides contain at least 50% long chain polyunsaturated fatty acids with at least 18 carbon atoms.

18. The composition according to claim 15, wherein the triglycerides are selected from vegetable oils, marine oils, and mixtures thereof, selected from soy oil, corn oil, olive oil, sunflower oil, sesame oil, safflower oil, wheat germ oil, arachidic oil, evening primrose oil, egg oil, fish oil, algal oil and mixtures thereof.

19. The composition according to claim 15, wherein cholesterol and precursors thereof are selected from cholesterol and cholesterylesters and/or salts thereof.

20. The composition according to claim 15, wherein the weight ratio cholesterol to phospholipids to triglycerides is 1:3-20:3-90.

21. The composition according to claim 20, wherein the weight ratio cholesterol to phospholipids to triglycerides is 1:6-16:6-60.

22. The composition according to claim 15, wherein the weight ratio cholesterol to phospholipids to triglycerides is preferably 1:20-80:3-80.

23. The composition according to claim 22, wherein the weight ratio cholesterol to phospholipids to triglycerides is 1:20-75:20-75.

24. The composition according to claim 15, wherein the composition contains egg, an egg lipid fraction, or an egg protein fraction.

25. The composition according to claim 15, wherein the composition further contains immunoglobulins.

26. The composition according to claim 15, wherein the composition contains soy lecithin.

27. The composition according to claim 15, wherein the composition is an oral feeding, tube feeding or infant formula.

28. The composition according to claim 15, wherein the composition further contains one or more fat soluble substances, selected from vitamin K, ubiquinones, carotenoids such as vitamin A, specific fatty acids such as conjugated linoleic acid, lipoic acid, vitamin D and mixtures thereof.

29. An enteral composition comprising: 45% to 91% by weight of the composition of phospholipids; from 0.5% to 8% by weight of the composition of cholesterol or cholesterylester and/or salt thereof; an amount of triglycerides such that the weight ratio of cholesterol to phospholipids to triglycerides is 1:3-80:3-90; and an amount of egg fraction, wherein, the phospholipids, the cholesterol or cholesterylester and/or salt thereof, the triglycerides, and the egg fraction are present in amounts sufficient to increase production of chylomicrons in a subject.

* * * * *